(12) United States Patent
Panoskaltsis-Mortari et al.

(10) Patent No.: US 8,609,412 B2
(45) Date of Patent: Dec. 17, 2013

(54) MAPC GENERATION OF LUNG TISSUE

(75) Inventors: Angela Panoskaltsis-Mortari, Woodbury, MN (US); Bruce Blazar, Golden Valley, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 1672 days.

(21) Appl. No.: 11/587,511

(22) PCT Filed: Apr. 21, 2005

(86) PCT No.: PCT/US2005/013651
§ 371 (c)(1),
(2), (4) Date: Aug. 13, 2007

(87) PCT Pub. No.: WO2005/113748
PCT Pub. Date: Dec. 1, 2005

(65) Prior Publication Data
US 2008/0274088 A1    Nov. 6, 2008

Related U.S. Application Data

(63) Continuation-in-part of application No. 11/084,256, filed on Mar. 21, 2005, which is a continuation of application No. 10/048,757, filed as application No. PCT/US00/21387 on Aug. 4, 2000, now Pat. No. 7,015,037, application No. 11/587,511, which is a continuation-in-part of application No. 10/467,963, filed as application No. PCT/US02/04652 on Feb. 14, 2002.

(60) Provisional application No. 60/268,786, filed on Feb. 14, 2001, provisional application No. 60/269,062, filed on Feb. 15, 2001, provisional application No. 60/310,625, filed on Aug. 7, 2001, provisional application No. 60/343,386, filed on Oct. 25, 2001, provisional application No. 60/164,650, filed on Nov. 10, 1999, provisional application No. 60/147,324, filed on Aug. 5, 1999, provisional application No. 60/564,628, filed on Apr. 21, 2004.

(51) Int. Cl.
*C12N 5/00* (2006.01)

(52) U.S. Cl.
USPC .......................... 435/377; 435/375; 435/366

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. |
| 5,635,386 A | 6/1997 | Palsson et al. |
| 5,827,735 A | 10/1998 | Young et al. |
| 6,090,625 A | 7/2000 | Abuljadayel |
| 6,653,134 B2 | 11/2003 | Prockop et al. |
| 6,777,231 B1 | 8/2004 | Katz et al. |
| 7,045,148 B2 | 5/2006 | Hariri |
| 7,056,738 B2 | 6/2006 | Prockop et al. |
| 7,229,827 B2 | 6/2007 | Kim et al. |
| 7,311,905 B2 | 12/2007 | Hariri |
| 2001/0033834 A1 | 10/2001 | Wilkison et al. |
| 2001/0046489 A1 | 11/2001 | Habener et al. |
| 2002/0061587 A1 | 5/2002 | Anversa |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2004/0235165 A1 | 11/2004 | Prockop et al. |
| 2005/0169896 A1 | 8/2005 | Li et al. |
| 2006/0177925 A1 | 8/2006 | Rosenberg et al. |

FOREIGN PATENT DOCUMENTS

| | | |
|---|---|---|
| CA | 2191655 | 6/1997 |
| EP | 0627487 | 5/1993 |
| WO | WO-95/03062 | 7/1993 |
| WO | WO-95/10599 | 10/1993 |
| WO | WO 96/23870 | 8/1996 |
| WO | WO-99/27076 | 11/1997 |
| WO | WO-99/35243 | 1/1998 |
| WO | WO-99/11758 | 3/1999 |
| WO | WO 99/16863 | 4/1999 |
| WO | WO 99/35243 | 7/1999 |
| WO | WO 01/04268 | 1/2001 |
| WO | WO 01/08691 | 2/2001 |
| WO | WO 01/21766 | 3/2001 |
| WO | WO 01/21767 | 3/2001 |
| WO | WO 01/62901 | 8/2001 |
| WO | WO 02/08388 | 3/2002 |
| WO | WO 02/34890 | 5/2002 |
| WO | WO 02/064748 | 8/2002 |
| WO | WO-02064748 A2 | 8/2002 |
| WO | WO 03/080649 | 10/2003 |
| WO | WO-03080649 A2 | 10/2003 |
| WO | WO 2004/015091 | 2/2004 |
| WO | WO-2004015091 A2 | 2/2004 |
| WO | WO-2005113748 A2 | 12/2005 |
| WO | WO-2005113748 A3 | 12/2005 |

OTHER PUBLICATIONS

Ali, N. N., et al., "Derivation of Type II Alveolar Epithelial Cells from Murine Embryonic Stem Cells", *Tissue Engineering, Larchmont*, vol. 8 (4), (Aug. 2002),541-550.

Ben-Shushan, Etti, et al., "Rex-1, a Gene Encoding a Transcription Factor Expressed in the Early Embryo, is Regulated via Oct-3/4 and Oct-6 Binding to an Octamer Site and a Novel Protein, Rox-1, Binding to an Adjacent Site", *Molecular & Cellular Biology*, 18(4), (Apr. 1998),1866-1878.

(Continued)

*Primary Examiner* — Blaine Lankford
(74) *Attorney, Agent, or Firm* — Tarolli, Sundheim, Covell & Tummino

(57) ABSTRACT

The present invention relates to methods of improving function in lung tissue by administering a population of multipotent adult progenitor cells ("MAPCs") or differentiated progeny thereof.

4 Claims, 2 Drawing Sheets

(56) References Cited

OTHER PUBLICATIONS

Cassiede, Pierre, et al., "Osteochondrogenic potential of marrow mesenchymal progenitor cells exposed to TGF-B1 or PDGF-BB as assay invivo and in vitro", *J. of Bone and Mineral REs.*, 11 (9), (1996),pp. 1264-1273.

Hilton, Douglas J., et al., "Distribution and Comparison of Receptors for Leukemia Inhibitory Factor on Murine Hemopoietic and Hepatic cells", *J. of Cellular Physiology*, 146 (2), (1991),pp. 207-215.

Jiang, Y., et al., "Pluripotency of Mesenchymal Stem Cells Derived From Adult Marrow", *Nature*, 418(6893), (Jul. 4, 2002),41-49.

Lennon, Donald P., et al., "A Chemically defined medium supports in vitro proliferation and maintains the osteochondral potential of rat marrow-derived mesenchymal stem cells", *Experimental Cell Res.*, 219 (1), (1995),pp. 211-222.

Pittenger, Mark F., "Multilineage ptoential of adult human mesenchymal stem cells", *Science, US, Amer. Assoc. for the Advancement of Science*, 284 (5411), (Apr. 2, 1999),pp. 143-147.

Raptis, A., et al., "Polymorhoism in CD33 and CD34 genes: a source of minor histocompatibility antigens on haemopoietic progenitor cells?", *British J. of Haematology*, 102 (5), (1998),pp. 1354-1358.

Rosfjord, Edward, et al., "The octamer motif present in the REX-1 promoter binds OCT-1 and OCT-3 expressed by EC cells and eS cells", *Biochem. and Biophysical Res. Comm.*, 203 (3), (1994),pp. 1795-1802.

Rosner, Mitchell H., et al., "Oct-3 is a maternal factor required for the first mouse embryonic division", *Cell*, 64 (6), (1991),pp. 1103-1110.

Cambrex specimens, "Poietics Human Mesenchymal Stem Cell Systems," Cambrex BioScience Walkersville, Inc, (2005).

Prockop, D., "Marrow stromal cells as stem cells for nonhematopoietic tissues" Science; 276:71-74 (1997).

Bjornson et al., "Turning brain into blood: a hematopoletic fate adopted by adult neural stem cells in vivo" Science; 283:534-537 (1999).

Reyes at al., "Purification and ex vivo expansion of postnatal human marrow mesodermal progenitor cells" Blood; 98:2615-25 (2001).

Bouwens, L., "Transdifferentiation versus stem cell hypothesis for the regeneration of islet beta-cells in the pancreas" Microscopy Research and Technique; 43:332-336 (1998).

Reyes et al., "Origin of endothelial progenitors in human postnatal bone marrow" J. Clin. Invest.; 109:1-10 (2002).

Reyes at al., "Characterization of multilineage mesodermal progenitor cells in adult marrow" Abstract No. 124, American Society for Hematology (2001).

Reyes et al., "Turning marrow into brain: generation of glial and neuronal cells from adult bone marrow mesenchymal stem cells" Abstract No. 1676, American Society for Hematology (2001).

Reyes et al., "Skeletal smooth and cardiac muscle differentiation from single adult marrow derived mesodermal progenitor cells" Abstract No. 2610, American Society for Hematology (2001).

Reyes et al., "In vitro and in vivo characterization of neural cells derived from mesenchymal stem cells" Abstract 2126, American Society for Hematology (2001).

Reyes et al., "Endothelial cells generated from human marrow derived mesenchymal stem cells (MSC)" Abstract No. 2276, American Society for Hematology (2001).

Zhao et al., "Immunohistochemical identification of multipotent adult progenitor cells from human bone marrow after transplantation into the rat brain" Brain Res Brain Res Protoc; 11:38-45 (2003).

Jiang et al., "Multipotent progenitor cells can be isolated from postnatal murine bone marrow, muscle, and brain" Exp. Hematol.; 30:896-904 (2002).

Jiang et al., "Pluripotency of mesenchymal stem cells derived from adult marrow" Nature; 418:41-49 (2002).

Schwartz, R., "Multipotent adult progenitor cells from bone marrow differentiate into hepatocyte-like cells" J Clin Invest.; 109:1291-1302 (2002).

Zhao et al., "Human bone marrow stem cells exhibit neural phenotypes and ameliorate neurological deficits after grafting into the ischemic brain of rats" Exp Neurol; 174:11-20 (2002).

Lamming et al., "Spontaneous circulation of myeloid-lymphoid-initiating cells and SCID-repopulating cells in sickle cell crisis" J. Clin. Invest.; 111:811-819 (2003).

Qi et al., "Identification of genes responsible for osteoblast differentiation from human mesodermal progenitor cells" Nat. Acad. Sci. USA; 100:3305-3310 (2003).

Verfaillie, C. "Investigator Profile" Journal of Hematotherapy and Stem Cell Research; 11:441-444 (2002).

Verfaillie et al., "Stem cells: hype and reality" Hematology (Am Soc Hematol Educ Program); 369-391 (2002).

Verfaille, C., "Optimizing hematopoietic stern cell engraftment: a novel role for thrombopoeitin" J. Clin. Invest.; 110:303-304 (2002).

Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol; 30:582-589 (2002).

Lewis et al., "Multi-lineage expansion potential of primitive hematopoietic progenitors: superiority of umbilical cord blood compared to mobilized peripheral blood" Exp. Hematol.; 28:1087-1095 (2002).

Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).

Punzel et al., "The myeloid-lymphoid initiating cell (ML-IC) assay assesses the fate of multipotent human progenitors in vitro" Blood; 93:3750-3756 (1999).

Roy et al., "Expression and function of cell adhesion molecules on fetal liver, cord blood and bone marrow hematopoietic progenitors: implications for anatomical localization and developmental stage specific regulation of hematopoiesis" Exp. Hematol; 27:302-312 (1999).

Miller et al., "Ex vivo culture of CD34+/Lin-/DR- cells in stroma-derived soluble factors, interleukin-3, and macrophage inflammatory protein-1 alpha maintains not only myeloid but also lymphoid progenitors in a novel switch culture assay" Blood; 15:4516-4522 (1998).

Verfaillie, C., "Stem cells in chronic myelogenous Leukemia" Hematol. Oncol, Clin. North Am.; 11:1079-1114 (1997).

Prosper et al., "Phenotypic and functional characterization of long-term culture-initiating cells present in peripheral blood progenitor collections of normal donors treated with granulocyte colony-stimulating factor" Blood; 15:2033-2042 (1996).

Lodie et al., "Systematic analysis of reportedly distinct populations of multipotent bone marrow-derived stem cells reveals a lack of distinction" Tissue Engineering; 8:739-751 (2002).

Pagen Westphal, S., "Adult bone marrow eyed as source of stem cells" Boston Globe, Jan. 24, 2002.

Pagen Westphal, S., "Ultimate stem cell discovered" New Scientist, Jan. 23, 2002.

Wade et al., "Scientists herald a versatile adult cell" The New York Times on the Web, Jan. 25, 2002.

Rosford et al., "The octamer motif present in the Rex-1 promoter binds Oct-1 and Oct-3 expressed by EC cells and ES cells" Biochem. Biophys. Res. Comm.; 203:1795-1802 (1994).

Rosner et al., "Oct-3 is a maternal factor required for the first mouse embryonic division" Cell; 64:1103-1110 (1991).

Pittenger et al., "Multilineage potential of adult human mesenchymal stem cells"; Science; 284:143-147 (1999).

Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mot. Cell Biol.; 18:1866-1878 (1998).

Reyes et al., "Characterization of multipotent adult progenitor cells, a subpopulation of mesenchymal stem cells" Annals of the New York Academy of Science; 938:231-235 (2001).

Anjos-Afonso and Bonnet, "Nonhematopoietic/endothelial SSE-1+ cells define the most primitive progenitors in the adult murine bone marrow mesenchymal compartment" Blood; 109:1298-1306 (2007).

Bertani et al., "Neurogenic potential of human mesenchymal stem cells revisited: analysis by immunostaining, time-lapse video and microarray" J Cell Sci.; 118:3925-36 (2005).

(56) References Cited

OTHER PUBLICATIONS

Bodnar et al., "Extension of life-span by introduction of telomerase into normal human cells" Science; 279:349-352 (1998).
Horwitz et al., "Clarification of the nomenclature for MSC: the international society for cellulartherapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stern cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmentaf manipulation in vitro" Stem Cells; 23:594-604 (2005).
Sanchez-Ramos et al., "Adult bone m arrow stromal cells differentiate into neural cells in vitro" Exp. Neural.; 164:247-56 (2000).
Eglitis et al., "Hematopoietic cells differentiate into both microglia and macroglia in the brain of adult mice" Proc. Natl. Acad. Sci, USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office, Office Action dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action dated Apr. 7, 2008 in related U.S. Appl. No. 11/151,689.
U.S. Patent and Trademark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action dated Apr. 3, 2007 in related U.S. Appl. No. 11/238,234.
U.S. Patent and Trademark Office, Office Action dated Oct. 7, 2008 in related U.S. Appl. No. 11/238,234.
Communication, filed Oct. 2, 2007 in related U.S. Appl. No. 11/238,234.
Information Disclosure Statement, Second Communication and PTO/SB/08b, filed Dec. 24, 2008 in related U.S. Appl. No. 11/238,234.
International Search Report for priority application PCT/US2005/013651, dated Dec. 6, 2005.
Ali et al, "Derivation of Type II Alveolar Epithelial Cells From Murine Embryonic Stem Cells" Tissue Engineering 8:541-550 (2002).

1 = B6 lung
2 = MAPCs w/SAGM
3 = MAPCs
4 = no DNA

MAPC GENERATION OF LUNG TISSUE

RELATED APPLICATIONS

This application is a nationalization under 35 U.S.C. §371 of PCT/US2005/013651, filed Apr. 21, 2005 and published in English as WO 2005/113748 on Dec. 1, 2005 which claims priority under 35 U.S.C. §119(e) from U.S. Provisional Application Ser. No. 60/564,628, filed Apr. 21, 2004; this application is also a continuation-in-part of U.S. application Ser. No. 11/084,256, filed Mar. 21, 2005, which is a continuation of U.S. application Ser. No. 10/048,757 (now issued U.S. Pat. No. 7,015,037) filed Feb. 1, 2002 which is a U.S. National Stage Application of PCT/US00/21387 filed Aug. 4, 2000 and published in English as WO 01/11011 on Feb. 15, 2001, which claims priority under 35 U.S.C. §119(e) from U.S. Provisional Application Ser. No. 60/147,324 filed Aug. 5, 1999 and 60/164,650 filed Nov. 10, 1999 and this application is a continuation-in-part of U.S. application Ser. No. 10/467,963 filed on Aug. 11, 2003 which is a U.S. National Stage Application of PCT/US02/04652 filed Feb. 14, 2002 and published in English as WO 02/064748 on Aug. 22, 2002, which claims priority under 35 U.S.C. §119(e) from U.S. Provisional Application Ser. No. 60/268,786 filed Feb. 14, 2001; 60/269,062 filed Feb. 15, 2001; 60/310,625 filed Aug. 7, 2001; and 60/343,386 filed Oct. 25, 2001, the contents of the applications and publications are incorporated herein by reference in their entireties.

FEDERALLY SPONSORED RESEARCH OR DEVELOPMENT

This work was funded by United States Grant No. RO1-HL55209-05 from the National Institutes of Health. The government may have certain rights to this invention.

FIELD OF THE INVENTION

The present invention relates to methods of alleviating the symptoms of lung damage or abnormal lung function by administering multipotent adult progenitor cells ("MAPCs") or differentiated progeny thereof, such as MAPC-derived alveolar type II epithelial cells.

BACKGROUND OF THE INVENTION

Acute pulmonary dysfunction post-bone marrow transplant (BMT) is a relatively frequent and severe complication of allogeneic BMT occurring in the first 100 days with an incidence of 35% in unrelated donor (URD) and 22% in peripheral blood stem cell transplants. Idiopathic Pneumonia Syndrome (IPS) injury represents a subset of these patients that have diagnostic criteria including signs and symptoms of pneumonia, evidence for nonlobar radiographic infiltrates, abnormal pulmonary function, and absence of lower respiratory tract infection. Conditioning regimen injury is the highest contributory factor for IPS. A multivariant analysis of the Seattle data indicated a hazard ratio of 9.3 for IPS in patients >age 40 who received 12 Gray total body irradiation (TBI) as compared to those receiving non-myeloablative transplants. Although acute graft versus host disease (GVHD) is a risk factor, IPS cannot be attributable simply to an alloresponse in humans. The incidence of IPS in allotransplants ranges from 5-20%. A recent large retrospective analysis indicated a rate of 8.4% in conventional transplant recipients. In most studies, the incidence of IPS in humans has been shown to be higher in recipients given more intense conditioning regimens and in recipients of allogeneic vs autologous BMT. Because of the association of alloresponses with IPS injury, the incidence of IPS will probably increase as the donor pool is extended to include BMT from unrelated donors. Once IPS has developed, the death rate is very high (usually ≥75%) and time to mortality is rapid (usually 2 weeks).

Therapeutic strategies are limited and in general consist of supportive care, mechanical ventilation and high dose steroids, which are not sufficient to prevent the high mortality rate. Acute IPS injury also may set the stage for bronchiolitis obliterans (BO) or bronchiolitis obliterans with organizing pneumonia (BOOP) which occur in 5-25% of long-term allo-BMT survivors and has been linked to chronic GVHD. Some cases of IPS, BO and BOOP will result in fibrosis which may occur within several weeks after onset. While tumor necrosis factor (TNF) neutralization has had some success in IPS management, a need for more effective clinical treatment exists.

Stem Cells

The quintessential stem cell is the embryonal stem (ES) cell, as it has unlimited self-renewal and can differentiate into all tissue types. ES cells are derived from the inner cell mass of the blastocyst, or primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in post-natal animals, ES and EG cells generate teratomas.

ES (and EG) cells can be identified by positive staining with antibodies to SSEA 1 (mouse) and SSEA4 (human). At the molecular level, ES and EG cells express a number of transcription factors specific for these undifferentiated cells. These include oct-4 and rex-1. Also found are the LIF-R and the transcription factors sox-2 and rox-1. Rox-1 and sox-2 are also expressed in non-ES cells. Another hallmark of ES cells is the presence of telomerase, which provides these cells with an unlimited self-renewal potential in vitro.

Oct-4 is a transcription factor expressed in the pregastrulation embryo, early cleavage stage embryo, cells of the inner cell mass of the blastocyst, and in embryonic carcinoma (EC) cells (Nichols J., et al (1998) *Cell* 95:379-91). Oct-4 is downregulated when cells are induced to differentiate in vitro. In the adult animal oct-4 is only found in germ cells. Several studies have shown that oct-4 is required for maintaining the undifferentiated phenotype of ES cells and plays a major role in determining early steps in embryogenesis and differentiation. Oct-4, in combination with Rox-1, causes transcriptional activation of the Zn-finger protein rex-1, which is also required for maintaining ES in an undifferentiated state ((Rosfjord E, Rizzino A. (1997) *Biochem Biophys Res Commun* 203:1795-802; Ben-Shushan E, et al (1998) *Mol Cell Biol* 18:1866-78)). Likewise, sox-2, is needed together with oct-4 to retain the undifferentiated state of ES/EC (Uwanogho D et al (1995) *Mech Dev* 49:23-36) and to maintain murine (but not human) ES cells. Human or murine primordial germ cells require the presence of LIF.

The oct 4 gene (oct 3 in humans) is transcribed into at least two splice variants in humans, oct3A and oct3B. The oct3B splice variant is found in many differentiated cells whereas the oct3A splice variant (also previously designated oct3/4) is reported to be specific for the undifferentiated embryonic stem cell. See Shimozaki et al. *Development* 130:2505-12 (2003).

Adult stem cells have been identified in most tissues. Hematopoietic stem cells are mesoderm-derived and have been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages. Hematopoietic stem cells can repopulate the erythroid, neutrophil-macrophage, megakaryocyte and lymphoid hemopoietic cell pool. Stem cells which differentiate only to form cells of hematopoietic lineage, however, are unable to provide a source of cells for repair of other damaged tissues, for example, heart.

Neural stem cells were initially identified in the subventricular zone and the olfactory bulb of fetal brain. Several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells.

Mesenchymal stem cells, originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. Of the many mesenchymal stem cells that have been described, all have demonstrated limited differentiation to form only those differentiated cells generally considered to be of mesenchymal origin. To date, the best characterized mesenchymal stem cell reported is the cell isolated by Pittenger, et al. (1999) and U.S. Pat. No. 5,827,740 ($SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD^{45}-$). This cell is capable of differentiating to form a number of cell types of mesenchymal origin, but is apparently limited in differentiation potential to cells of the mesenchymal lineage, as the team who isolated it noted that hematopoietic cells were never identified in the expanded cultures.

SUMMARY OF THE INVENTION

MAPC is an acronym for multipotent adult progenitor cells (a non ES, non EG, non germ cell) that has the capacity to differentiate into cell types of all three primitive germ layers (ectodermal, endodermal and mesodermal). Genes that have been associated with the undifferentiated state of ES cells were also found in MAPCs (oct 3/4, rex-1, telomerase, rox-1, sox-2).

Biologically and antigenically distinct from MSC, MAPC represents a more primitive progenitor cell population than the MSC and demonstrates differentiation capability encompassing the epithelial, endothelial, neural, myogenic, hematopoeitic, osteogenic, hepatogenic, chondrogenic and adipogenic lineages (Verfaillie, C. M. (2002) *Trends Cell Biol.* 12(11): p. 502-8, Jahagirdar, B. N., et al. (2001) *Exp Hematol,* 29(5): p. 543-56). MAPCs thus represent a new class of adult stem cell that emulate the broad biological plasticity characteristic of ES cells, while maintaining the other characteristics that make adult stem cells appealing. For example, MAPCs are capable of indefinite culture without loss of their differentiation potential and show efficient, long term, engraftment and differentiation along multiple developmental lineages in NOD-SCID mice without evidence of teratoma formation (Reyes, M. and C. M. Verfaillie (2001) *Ann N Y Acad Sci,* 938: p. 231-3; discussion 233-5).

It has now been demonstrated MAPCs, previously named multipotent adult stem cells (MASCs), are capable of forming functional alveolar type II epithelial cells. Therefore, the present invention relates to compositions comprising and methods of providing alveolar type II epithelial cells or otherwise treating lung damage or abnormal lung function. Such compositions and methods are useful in the treatment of lung disorders, such as Idiopathic Pneumonia Syndrome.

In one embodiment, the invention provides methods to treat damaged lung tissue comprising administering to subject in need thereof an effective amount of alveolar type II epithelial cells produced by differentiating MAPCs into alveolar type II epithelial cells ex vivo.

In another embodiment, the invention provides a method to treat damaged lung tissue comprising administering to a subject in need thereof an effective amount of MAPCs.

In another embodiment, the invention provides a method to treat a lung disorder comprising administering to a subject in need thereof an effective amount of alveolar type II epithelial cells produced by differentiating MAPCs into alveolar type II epithelial cells ex vivo.

In another embodiment, the method to treat a lung disorder comprises administering to a subject in need thereof an effective amount of MAPCs.

In one embodiment, the damaged lung tissue or the lung disorder is a result of chemotherapy, irradiation, smoke or physical injury or a disorder selected from the group consisting of acute lung injury, acute respiratory distress syndrome, idiopathic pneumonia syndrome, acute pulmonary dysfunction, abnormal pulmonary function, asthma, cystic fibrosis, organizing pneumonia or cancer.

In another embodiment, the invention provides a method to provide alveolar type II epithelial cells comprising administering to a subject alveolar type II epithelial cells produced by differentiating MAPCs into alveolar type II epithelial cells ex vivo.

In another embodiment, the invention provides a method to provide alveolar type II epithelial cells comprising administering to a subject MAPCs.

In one embodiment, the alveolar type II epithelial cells provide one or more of: preservation and/or regeneration of lung tissue, secretion of surfactant, engraftment in lung tissue, reepithelialization of alveolar basement membrane in lung tissue and/or provide lung alveolar epithelium. In another embodiment, the administration of MAPCs results in one or more of: preservation and/or regeneration of lung tissue, secretion of surfactant, engraftment in lung tissue, reepithelialization of alveolar basement membrane in lung tissue and/or lung alveolar epithelium.

In another embodiment, the invention provides a method to produce alveolar type II epithelial cells in vitro by differentiating cultured MAPCs with alveolar type II epithelial cell differentiation factors. In one embodiment, the differentiated alveolar type II epithelial cells are isolated. In another embodiment, the differentiated alveolar type II epithelial cells are grown in culture medium.

In another embodiment, the invention provides a method to prepare a composition comprising mixing an effective therapeutic amount of alveolar type II epithelial cells with a pharmaceutically acceptable carrier, wherein the alveolar type II epithelial cells are produced by differentiating MAPCs to alveolar type II epithelial cells. Another embodiment provides a composition comprising alveolar type II epithelial cells and a pharmaceutically acceptable carrier.

Another embodiment provides the use of alveolar type II epithelial cells or MAPCs to prepare a medicament for treating damaged lung tissue. In one embodiment, the damage to the lung tissue is a result of chemotherapy, irradiation, smoke or physical injury or a disorder selected from the group consisting of acute lung injury, acute respiratory distress syndrome, idiopathic pneumonia syndrome, acute pulmonary dysfunction, abnormal pulmonary function, asthma, cystic fibrosis, organizing pneumonia or cancer.

Other aspects of the invention are described in or are obvious from the following disclosure, and are within the ambit of the invention.

BRIEF DESCRIPTION OF THE FIGURES

The following Detailed Description, given by way of example, but not intended to limit the invention to specific embodiments described, may be understood in conjunction with the accompanying drawings.

DETAILED DESCRIPTION OF THE INVENTION

Figure 1:
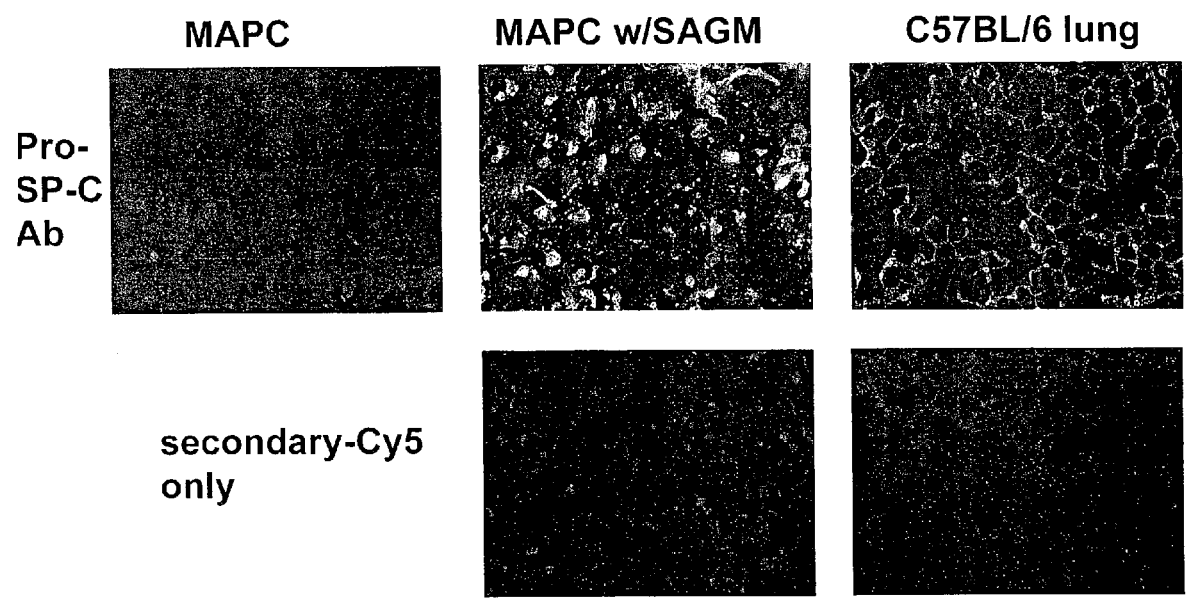
FIG. 1 depicts MAPCs that were cultured to promote differentiation to alveolar type II-like epithelial cells. MAPCs that were cultured in MAPC medium are shown in the upper left panel. MAPCs grown in SAGM are depicted in the upper middle panel, while normal mouse lung is also shown as a positive control (upper right panel).

MAPC have the ability to regenerate all primitive germ layers (endodermal, mesodermal, and ectodermal) in vitro and in vivo. In this context they are equivalent to embryonal stem cells, and distinct from mesenchymal stem cells, which are also isolated from bone marrow. The biological potency of these cells has been proven in various animal models, including mouse, rat, and xenogeneic engraftment of human stem cells in rats or NOD/SCID mice (Reyes, M. and C. M. Verfaillie (2001) *Ann N Y Acad Sci.* 938: p. 231-3; discussion 233-5, Jiang, Y. et al. (2002) *Exp Hematol.* 30(8): p. 896-904). In an elegant demonstration of the clonal potency of this cell population, single genetically marked MAPC were injected into mouse blastocysts, blastocysts implanted, and embryos developed to term (Jiang, Y. et al. (2002) *Nature* 418(6893): p. 41-9.). Post-natal analysis in highly chimeric animals shows reconstitution of all tissues and organs, including liver. No abnormalities or organ dysfunction were observed in any of these animals.

DEFINITIONS

As used herein, the terms below are defined by the following meanings.

"MAPC" is an acronym for a multipotent adult progenitor cell. It refers to a non-embryonic stem cell that can differentiate to cells of all three germ layer lineages (i.e., endoderm, mesoderm and ectoderm). Like embryonic stem cells, MAPCs express oct-3/4 (i.e., oct-3A), rex-1, rox-1, sox-2 and telomerase. MAPC may express SSEA-4 and nanog. The term "adult" with respect to MAPC is non-restrictive. It refers to a non-embryonic somatic cell.

MAPCs constitutively express Oct 3/4 and high levels of telomerase (Jiang, Y. et al (2002) *Nature* 418 (6893):41; Exp Hematol. 30(8):896. MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease, or, as disclosed below, may contribute to preservation of healthy cells or production of new cells in tissue.

"Multipotent," with respect to MAPC is not limiting. It refers to the ability to give rise to cells having lineages of all three primitive germ layers (i.e., endoderm, mesoderm and ectoderm) upon differentiation.

"Progenitor cells" are cells produced during differentiation of a stem cell that have some, but not all, of the characteristics of their terminally differentiated progeny. Defined progenitor cells, such as "endothelial progenitor cells," are committed to a lineage, but not to a specific or terminally differentiated cell type. The term "progenitor" as used in the acronym "MAPC" does not limit these cells to a particular lineage.

"Self-renewal" refers to the ability to produce replicate daughter stem cells having differentiation potential that is identical to those from which they arose. A similar term used in this context is "proliferation."

"Expansion" refers to the propagation of a cell or cells without differentiation.

"Engraft" or "engraftment" refers to the process of cellular contact and incorporation into an existing tissue of interest in vivo.

"Alveolar type II epithelial cells" refers to both alveolar type II epithelial and alveolar type II epithelial-like cells (e.g., pulmonary epithelial cells with biochemical characteristics similar to those of alveolar type II epithelial cells).

The term "isolated" refers to a cell or cells which are not associated with one or more cells or one or more cellular components that are associated with the cell or cells in vivo. An "enriched population" means a relative increase in numbers of MAPC relative to one or more non-MAPC cell types in vivo or in primary culture.

"Cytokines" refer to cellular factors that induce or enhance cellular movement, such as homing of MAPCs or other stem cells, progenitor cells or differentiated cells. Cytokines may also stimulate such cells to divide.

"Differentiation factors" refer to cellular factors, preferably growth factors or angiogenic factors, that induce lineage commitment.

A "subject" is a vertebrate, preferably a mammal, more preferably a human. Mammals include, but are not limited to, humans, farm animals, sport animals, and pets. Subjects in need of treatment by methods of the present invention include those suffering from a loss of function in lung tissue as a result of physical or disease related damage.

As used herein, "treat," "treating" or "treatment" includes treating, preventing, ameliorating, or inhibiting an injury or disease related condition and/or a symptom of an injury or disease related condition.

An "effective amount" generally means an amount which provides the desired local or systemic effect, such as enhanced performance. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, injury and/or disease or being treated and amount of time since the injury occurred or the disease began. One skilled in the art, specifically a physician, would be able to determine the number of cells that would constitute an effective dose.

"Co-administer" can include simultaneous and/or sequential administration of two or more agents.

Administered MAPCs may contribute to generation of new tissue by differentiating into lung cells (e.g., pulmonary epithelial cells) in vivo. Alternatively, or in addition, administered MAPCs may contribute to generation of new tissue by secreting cellular factors that aid in homing and recruitment of endogenous MAPCs or other stem cells, or other more differentiated cells, such as epithelial cells. Alternatively, or in addition, MAPCs may secrete factors that act on endogenous stem or progenitor cells in the target tissue causing them to differentiate in the target site, thereby enhancing function. Further, MAPCs may secrete factors that act on stem, progenitor, or differentiated cells in the target tissue, causing them to divide. Thus, MAPCs may provide benefit via trophic influences. Examples of trophic influences include limiting inflammatory damage, limiting vascular permeability, improving cell survival or homing of repair cells to sites of damage. Additionally, MAPC may also provide benefit by increasing capillary density and stimulating angiogenesis. This may be achieved by production of angiogenic factors, such as VEGF, or by differentiation of the MAPCs and inclusion in new vessel tissue, or both. Therapeutic benefit may be achieved by a combination of the above pathways.

The terms "comprises", "comprising", and the like can have the meaning ascribed to them in U.S. Patent Law and can mean "includes", "including" and the like. As used herein, "including" or "includes" or the like means including, without limitation.

ASPECTS OF THE INVENTION

Compositions and methods of the invention are directed to the formation and use of MAPCs and MAPC-derived lung alveolar epithelial cells (e.g., alveolar type II or type I epithelial cells) for the treatment lung diseases/disorders and/or repopulation of lung tissue. Lung disease/disorder is any disease or disorder where lung function is impaired. There are three general physiologic categories of lung diseases/disorders: 1) obstructive lung disease—a decrease in the exhaled air flow caused by a narrowing or blockage of the airways, such as with asthma, emphysema, and chronic bronchitis, 2) restrictive lung disease—a decrease in the total volume of air that the lungs are able to hold, and 3) a defect in the ability of the lung's air sac tissue to move oxygen into a subject's blood. Many lung diseases involve a combination of these categories, such as emphysema, which involves both airflow obstruction and oxygenation problems.

Lung diseases/disorders include, but are not limited to environmental lung disease, occupational lung disease (e.g., mesothioloma), asthma, BOOP, chronic bronchitis, COPD (chronic obstructive pulmonary disease), emphysema, interstitial lung disease, pulmonary fibrosis, sarcoidosis, asbestosis, aspergilloma, aspergillosis, aspergillosis—acute invasive, atelectasis, eosinophilic pneumonia, lung cancer, metastatic lung cancer, necrotizing pneumonia, pleural effusion, pneumoconiosis, pneumocystosis, pneumonia, pneumonia in immunodeficient patient, pneumothorax, pulmonary actinomycosis, pulmonary alveolar proteinosis, pulmonary anthrax, pulmonary arteriovenous malformation, pulmonary edema, pulmonary embolus, pulmonary histiocytosis X (eosinophilic granuloma), pulmonary hypertension, pulmonary nocardiosis, pulmonary tuberculosis, pulmonary veno-occlusive disease, and rheumatoid lung disease. These diseases can all cause damage/injury to lung tissue.

In one embodiment, diseases (e.g., pulmonary lung disease) or other insults causing injury to lung tissue include, but are not limited to Idiopathic Pneumonia Syndrome (IPS), chemotherapy, irradiation, physical injury (e.g., a wound due to physical trauma or from a surgical procedure), ARDS (acute respiratory distress syndrome), asthma, cystic fibrosis, organizing pneumonia (BOOP), acute pulmonary dysfunction, abnormal pulmonary dysfunction, acute lung injury, cancer and smoke (for example, from smoking, second hand smoke, environmental smoke or smoke inhalation (e.g., smoke from a fire)).

Recovery from, for example, acute lung injury generally results in the proliferation and differentiation of alveolar epithelial cells to re-epithelialize the alveolar basement membrane. The lung alveolar epithelium is formed by alveolar type II epithelial cells (located in corners of alveoli) and type I cells covering >90% of the alveolar surface. Alveolar type II epithelial cells are responsible for surfactant secretion, which is needed for maintaining surface tension, and are progenitors for alveolar type I epithelial cells. Alveolar type I epithelial cells have a fluid barrier function and facilitate gas exchange.

In addition to its role as a progenitor cell and as a source of surfactant, another function of the alveolar type II epithelial cell is active sodium transport, the driving force for vectorial fluid transport across the alveolar epithelium. The ability to remove edema fluid from the alveolar space is needed for the restoration of adequate gas exchange in the setting of alveolar flooding from several disorders, including congestive heart failure and acute respiratory distress syndrome.

There are many tests available to one of skill in the art to determine/test lung function. For example, pulmonary function tests (PFT) are tools that physicians use to gauge the ability of the lungs. Generally, there are three kinds of PFTs: 1) ones that measure how well the lungs exhale, 2) ones that measure how much air the lungs can inhale, and 3) ones that measure how effectively the lungs can transfer oxygen into the bloodstream. Each of these tests is used to determine different disorders/diseases, severity of the disease/disorder and/or the effectiveness of treatment. Additionally, these tests, and others, can be use to determine if there has been progress since initiation of treatment. Additional tests for these purposes include but are not limited to chest imaging (e.g., chest x-ray, computed tomography, magnetic resonance imaging, ultrasound, nuclear lung scanning or angiography), arterial blood gas study, lung volume and flow rate measurements, flow volume testing (with, for example, a spirometer), muscle strength assessment (e.g., the strength of the respiratory muscles), diffusing capacity measurement, positron emission tomography, thoracentesis, needle biopsy of the pleura or lung, bronchoscopy, bronchoalveolar lavage, transbronchial lung biopsy, transbronchial needle aspiration, thoracoscopy, mediastinoscopy, thoracotomy and/or suctioning.

Multipotent Adult Stem Cells

Human MAPCs are described in PCT/US00/21387 (published as WO 01/11011) and PCT/US02/04652 (published as WO 02/064748), the contents of which are incorporated herein by reference for their characterization of MAPCs. MAPCs have been identified in other mammals. Murine MAPCs, for example, are also described in PCT/US00/21387 (published as WO 01/11011) and PCT/US02/04652 (published as WO 02/064748). Rat MAPCs are also described in WO 02/064748.

Isolation and Growth

Methods of MAPC isolation for humans and mouse are known in the art. They are described in PCT/US00/21387 (published as WO 01/11011) and for rat in PCT/US02/04652 (published as WO 02/064748), and these methods, along with the characterization of MAPCs disclosed therein, are incorporated herein by reference.

MAPCs were initially isolated from bone marrow, but were subsequently established from other tissues, including brain and muscle (Jiang, Y., et al., 2002). Thus, MAPCs can be isolated from multiple sources, including bone marrow, placenta, umbilical cord and cord blood, muscle, brain, liver, spinal cord, blood or skin. For example, MAPCs can be derived from bone marrow aspirates, which can be obtained by standard means known to those of skill in the art (see, for example, Muschler, G. F., et al., 1997; Batinic, D., et al., 1990). It is therefore now possible for one of skill in the art to obtain bone marrow aspirates, brain or liver biopsies, and other organs, and isolate the cells using positive or negative selection techniques known to those of skill in the art, relying upon the genes that are expressed (or not expressed) in these cells (e.g., by functional or morphological assays such as those disclosed in the above-referenced applications, which have been incorporated herein by reference).

MAPCs from Human Marrow as Described in PCT/US00/21387

To select multipotent adult stem cells, bone marrow mononuclear cells were derived from bone marrow aspirates, which were obtained by standard means known to those of skill in the art (see, for example, Muschler, G. F. et al. (1997) *J. Bone Joint Surg. Am.* 79(11): 1699-709; Batinic, D. et al. (1990) *Bone Marrow Transplant.* 6(2):103-7). Multipotent adult stem cells are present within the bone marrow (or other organs such as liver or brain), but do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of CD45$^+$ and Gly-A$^+$ cells, and the remaining approximately 0.1% of marrow mononuclear cells were then recovered. Cells can also be plated in fibronectin-coated wells and cultured as described below for 2-4 weeks to deplete the cells of CD45$^+$ and Gly-A$^+$ cells.

Alternatively, positive selection can be used to isolate cells via a combination of cell-specific markers. Both positive and negative selection techniques are known to those of skill in the art, and numerous monoclonal and polyclonal antibodies suitable for negative selection purposes are also known in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al. (1983), *J. Immunol. Methods* 56: 269 (immunoaffinity chromatography), and Wysocki and Sato (1978) *Proc. Natl. Acad. Sci.* (*USA*) 75: 2844 (fluorescence-activated cell sorting).

Recovered CD45$^-$/GlyA$^-$ cells were plated onto culture dishes coated with 5-115 ng/ml (about 7-10 ng/ml can be used) serum fibronectin or other appropriate matrix coating. Cells were maintained in Dulbecco's Minimal Essential Medium (DMEM) or other appropriate cell culture medium, supplemented with 1-50 ng/ml (about 5-15 ng/ml can be used) platelet-derived growth factor-BB (PDGF-BB), 1-50 ng/ml (about 5-15 ng/ml can be used) epidermal growth factor (EGF), 1-50 ng/ml (about 5-15 ng/ml can be used) insulin-like growth factor (IGF), or 100-10,000 IU (about 1,000 IU can be used) LIF, with $10^{-10}$ to $10^{-8}$ M dexamethasone (or other appropriate steroid), 2-10 µg/ml linoleic acid, and 0.05-0.15 µM ascorbic acid. Other appropriate media include, for example, MCDB, MEM, IMDM, and RPMI. Cells can either be maintained without serum, in the presence of 1-2% fetal calf serum, or, for example, in 1-2% human AB serum or autologous serum.

MAPCs cultured at low density under the conditions described expressed the LIF-R, and did not or minimally express CD44 whereas cells cultured at high density, that have characteristics of MSC, lose expression of LIF-R but express CD44. 1-2% CD45$^-$GlyA$^-$ cells were CD44$^-$ and <0.5% CD45$^-$GlyA$^-$ cells were LIF-R$^+$. FACS selected cells were subjected to quantitative RT-PCR (real time PCR) for oct-4 mRNA. Oct-4 mRNA levels were 5 fold higher in CD45$^-$GlyA$^-$CD44$^-$ and 20 fold higher in CD45$^-$GlyA$^-$LIF-R$^+$ cells than in unsorted CD45$^-$GlyA$^-$ cells. Sorted cells were plated in MAPC culture with 10 ng/mL EGF, PDGF-BB and LIF. The frequency with which MAPC started growing was 30-fold higher in CD45$^-$GlyA$^-$LIF-R$^+$ cells and 3 fold higher in CD45$^-$GlyA$^-$CD44$^-$ cells than in unsorted CD45$^-$GlyA$^-$ cells.

In these studies, when re-seeded at <0.5×10$^3$ cells/cm$^2$, cultures grew poorly and died. When re-seeded at >10×10$^3$ cells/cm$^2$ every 3 days, cells stopped proliferating after <30 cell doublings and lost differentiation potential. When re-seeded at 2×10$^3$ cells/cm$^2$ every 3 days, >40 cell doublings were routinely obtained, and some populations have undergone >70 cell doublings. Cell doubling time 36-48 h for the initial 20-30 cell doublings. Afterwards cell-doubling time was extended to as much as 60-72 h. However, optimal density can vary depending on culture conditions. Density can be as low as about 200-500 cells/cm2. It is within the skill of the ordinary artisan to determine the optimal density for a given set of culture conditions.

Telomere length of MAPCs from 5 donors (age 2 years-55 years) cultured at reseeding densities of 2×10$^3$ cells/cm$^2$ for 23-26 cell doublings was between 11-13 KB. This was 3-5 KB longer than telomere length of blood lymphocytes obtained from the same donors. Telomere length of cells from 2 donors evaluated after 23 and 25 cell doublings, respectively, and again after 35 cells doublings, was unchanged. The karyotype of these MAPCS was normal.

Phenotype of Human MAPCs Under Conditions Described in PCT/US00/21387

Immunophenotypic analysis by FACS of human MAPCs obtained after 22-25 cell doublings indicated that the cells do not express CD31, CD34, CD36, CD38, CD45, CD50, CD62E and -P, HLA-DR, Muc18, STRO-1, cKit, Tie/Tek; and express low levels of CD44, HLA-class I, and β2-microglobulin, but express CD10, CD13, CD49b, CD49e, CDw90, Flk1 (N>10).

Once cells underwent >40 doublings in cultures re-seeded at about 2×10$^3$/cm$^2$, the phenotype became more homogenous and no cell expressed HLA class-I or CD44 (n=6). When cells were grown at higher confluence, they expressed high levels of Muc18, CD44, HLA class I and β2-microglobulin, which is similar to the phenotype described for MSC (N=8) (Pittenger (1999) *Science* 284: 143-147).

Immunhistochemistry showed that human MAPCs grown at about 2×10³/cm² seeding density express EGF-R, TGF-R1 and -2, BMP-R1A, PDGF-R1a and -B, and that a small subpopulation (between 1 and 10%) of MAPCs stain with anti-SSEA4 antibodies (Kannagi, R (1983) *EMBO J* 2:2355-61).

Using Clontech cDNA arrays the expressed gene profile of human MAPCs cultured at seeding densities of about 2×10³ cells/cm² for 22 and 26 cell doublings was found:

A. MAPCs do not express CD31, CD36, CD62E, CD62P, CD44-H, cKit, Tie, receptors for IL1, IL3, IL6, IL11, G CSF, GM-CSF, Epo, Flt3-L, or CNTF, and low levels of HLA-class-I, CD44-E and Muc-18 mRNA.

B. MAPCs express mRNA for the cytokines BMP1, BMP5, VEGF, HGF, KGF, MCP1; the cytokine receptors Flk1, EGF-R, PDGF-R1α, gp130, LIF-R, activin-R1 and -R2, TGFR-2, BMP-R1A; the adhesion receptors CD49c, CD49d, CD29; and CD10.

C. MAPCs express mRNA for hTRT and TRF1; the POU domain transcription factor oct-4, sox-2 (required with oct-4 to maintain undifferentiated state of ES/EC, Uwanogho D (1995) *Mech Dev* 49:23-36)), sox 11 (neural development), sox 9 (chondrogenesis) (Lefebvre V (1998) *Matrix Biol* 16:529-40); homeodeomain transcription factors: Hoxa4 and -a5 (cervical and thoracic skeleton specification; organogenesis of respiratory tract) (Packer AI (2000) *Dev Dyn* 17:62-74), Hox-a9 (myelopoiesis) (Lawrence H (1997) *Blood* 89:1922), Dlx4 (specification of forebrain and peripheral structures of head) (Akimenko M A (1994) *J Neurosci* 14:3475-86), MSX1 (embryonic mesoderm, adult heart and muscle, chondro- and osteogenesis) (Foerst-Potts L (1997) *Dev Dyn* 209:70-84), PDX1 (pancreas) (Offield M F (1996) *Development* 122:983-95).

D. Presence of oct-4, LIF-R, and hTRT mRNA was confirmed by RT-PCR.

E. In addition, RT-PCR showed that Rex-1 mRNA (required with oct-4 to maintain ES in an undifferentiated state) (Rosfjord E (1997) *Biochem Biophys Res Commun* 203:1795-802) and Rox-1 mRNA (required with oct-4 for transcription of Rex-1) (Ben-Shushan E (1998) *Cell Biol* 18:1866-78) are expressed in MAPCs.

oct-4, Rex-1 and Rox-1 are expressed in MAPCs derived from human and murine marrow and from murine liver and brain. Human MAPCs express the LIF-R and stain positive with SSEA-4. Initial experiments indicated that human MAPCs are enriched by selection of LIF-R⁺. Finally, oct-4, LIF-R, Rex-1 and Rox-1 mRNA levels were found to increase in human MAPCs cultures beyond 30 cell doublings, which resulted in phenotypically more homogenous cells. In contrast, MAPCs cultured at high density lost expression of these markers. This is associated with senescence before 40 cell doublings and loss of differentiation to cells other than chondroblasts, osteoblasts and adipocytes. Thus, the presence of oct-4, combined with Rex-1, Rox-1, sox-2, and the LIF-R are markers that correlate with presence of the most primitive cells in MAPCs cultures.

Culturing MAPCs as Described in PCT/US00/21387

MAPCs isolated as described herein can be cultured using methods disclosed herein and in PCT/US00/21387, which is incorporated by reference for these methods.

Additionally, the density at which MAPCs are cultured can vary from about 100 cells/cm² or about 150 cells/cm² to about 10,000 cells/cm², including about 200 cells/cm² to about 1500 cells/cm² to about 2000 cells/cm². The density can vary between species. Additionally, optimal density can vary depending on culture conditions and source of cells.

Also, effective atmospheric oxygen concentrations of less than about 10%, including about 5%, can be used at any time during the isolation, growth and differentiation of MAPCs in culture.

Briefly, for the culture of MAPCs, culture in low-serum or serum-free medium is preferred to maintain the cells in the undifferentiated state. Serum-free medium used to culture the cells, as described herein, is supplemented as described in Table 1.

TABLE 1

| Insulin | 10-50 μg/ml (10 μg/ml)* |
|---|---|
| Transferrin | 0-10 μg/ml (5.5 μg/ml) |
| Selenium | 2-10 ng/ml (5 ng/ml) |
| Bovine serum albumin (BSA) | 0.1-5 μg/ml (0.5 μg/ml) |
| Linoleic acid | 2-10 μg/ml (4.7 μg/ml) |
| Dexamethasone | 0.005-0.15 μM (.01 μM) |
| L-ascorbic acid 2-phosphate | 0.1 mM |
| Low-glucose DMEM (DMEM-LG) | 40-60% (60%) |
| MCDB-201 | 40-60% (40%) |
| Fetal calf serum | 0-2% |
| Platelet-derived growth | 5-15 ng/ml (10 ng/ml) |
| Epidermal growth factor | 5-15 ng/ml (10 ng/ml) |
| Insulin like growth factor | 5-15 ng/ml (10 ng/ml) |
| Leukemia inhibitory factor | 10-10,000 IU (1,000 IU) |

*Preferred concentrations are shown in parentheses.

Because MAPCs express the LIF-R and some cells express oct-4, it was tested whether addition of LIF would improve culture. Addition of 10 ng/mL LIF to human MAPCs did not affect short-term cell growth (same cell doubling time till 25 cell doublings, level of oct-4 expression). In contrast to what was seen with human cells, when fresh murine marrow mononuclear cells depleted on day 0 of CD45⁺ cells were plated in MAPC culture, no growth was seen. When murine marrow mononuclear cells were plated, and cultured cells 14 days later depleted of CD45⁺ cells, cells with the morphology and phenotype similar to that of human MAPCs appeared. This suggests that factors secreted by hemopoietic cells may be needed to support initial growth of murine MAPCs. When cultured with PDGF-BB and EFG alone, cell doubling was slow (>6 days) and cultures could not be maintained beyond 10 cell doublings. Addition of 10 ng/mL LIF significantly enhanced cell growth.

Once established in culture, cells can be frozen and stored as frozen stocks, using DMEM with 40% FCS and 10% DMSO. Other methods for preparing frozen stocks for cultured cells are also available to those of skill in the art.

Thus, MAPCs can be maintained and expanded in culture medium that is available to the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. Many media are also available as a low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used advantageously to supply the cells with the necessary trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin ($\alpha$, $\beta$, $\gamma$), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the stem cells in an undifferentiated, proliferative state, as leukemia inhibitory factor (LIF) has anti-differentiation properties. Often, supplementation of a defined concentration of LIF is all that is necessary to maintain stem cells in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

The maintenance conditions of stem cells can also contain cellular factors that allow stem cells, such as MAPCs, to remain in an undifferentiated form. Specifically, these cellular factors or components allow the stem cells to remain pluripotent, constitutively express Oct-4, maintain high levels of telomerase, and remain negative for CD44, CD45, HLA (i.e., MHC class I and MHC class II) expression. It is advantageous under conditions where the cell must remain in an undifferentiated state of self-renewal for the medium to contain epidermal growth factor (EGF), platelet derived growth factor (PDGF), leukemia inhibitory factor (LIF), and combinations thereof. It is apparent to those skilled in the art that supplements that allow the cell to self-renew but not differentiate must be removed from the culture medium prior to differentiation.

Stem cell lines and other fastidious cells often benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the invention envisions the use of FACS to identify and separate cells based on cell-surface antigen expression.

Administration of MAPCs

MAPCs, or their differentiated progeny, can be administered to a subject by a variety of methods available to the art, including but not limited to localized injection, catheter administration, systemic injection, intraperitoneal injection, parenteral administration, oral administration, intracranial injection, intra-arterial injection, intravenous injection, intraventricular infusion, intraplacental injection, intrauterine injection, surgical intramyocardial injection, transendocardial injection, transvascular injection, intracoronary injection, transvascular injection, intramuscular injection, surgical injection into a tissue of interest or via direct application to tissue surfaces (e.g., during surgery or on a wound).

Intravenous injection is the simplest method of cell administration; however a greater degree of dependence on homing of the stem cells is required for them to reach the tissue of interest (e.g., lung). Carefully controlled dosing, which is readily determined by one skilled in the art, enhances this method of administration.

MAPCs can be administered either peripherally or locally through the circulatory system. "Homing" of stem cells to the injured tissues would concentrate the implanted cells in an environment favorable to their growth and function. Pretreatment of a patient with cytokine(s) to promote homing is another alternative contemplated in the methods of the present invention. Where homing signals may be less intense, injection of the cells directly into the lung may produce a more favorable outcome. Certain cytokines (e.g., cellular factors that induce or enhance cellular movement, such as homing of MAPCs or other stem cells, progenitor cells or differentiated cells) can enhance the migration of MAPCs or their differentiated counterparts to the site of damaged lung tissue. Cytokines include, but are not limited to, stromal cell derived factor-1 (SDF-1), stem cell factor (SCF) and granulocyte-colony stimulating factor (G-CSF). Cytokines also include any which promote the expression of endothelial adhesion molecules, such as ICAMs, VCAMs, and others, which facilitate the homing process.

Differentiation of MAPCs to a phenotype characteristic of lung tissues can be enhanced when differentiation factors are employed, e.g., factors promoting lung formation.

Viability of newly forming tissues can be enhanced by angiogenesis. Factors promoting angiogenesis include but are not limited to VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol, nicotinic amide.

Factors that decrease apoptosis can also promote the formation of new tissue, such as lung epithelium. Factors that decrease apoptosis include but are not limited to β-blockers, angiotensin-converting enzyme inhibitors (ACE inhibitors), AKT, HIF, carvedilol, angiotensin II type 1 receptor antagonists, caspase inhibitors, cariporide, and eniporide.

Exogenous factors (e.g., cytokines, differentiation factors (e.g., cellular factors, preferably growth factors or angiogenic factors that induce lineage commitment), angiogenesis factors and anti-apoptosis factors) can be administered prior to, after or concomitantly with MAPCs or their differentiated progeny (e.g., alveolar type II epithelial or epithelial like cells). For example, a form of concomitant administration would comprise combining a factor of interest in the MAPC suspension media prior to administration. Doses for administration(s) are variable and may include an initial administration followed by subsequent administrations.

A method to potentially increase cell survival is to incorporate MAPCs or other cells of interest into a biopolymer or synthetic polymer. Depending on the patient's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included cytokines, differentiation factors, angiogenesis factors and/or anti-apoptosis factors. Additionally, these could be in suspension. Another alternative is a three-dimension gel with cells entrapped within the interstices of the cell biopolymer admixture. Again cytokines, differentiation factors, angiogenesis factors and/or anti-apoptosis factors could be included within the gel. These could be deployed by injection via various routes described herein, via catheters or other surgical procedures.

In current human studies of autologous mononuclear bone marrow cells, empirical doses ranging from 1 to $4 \times 10^7$ cells have been used. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and most preferably, $3 \times 10^7$ stem cells and optionally, 50 to 500 µg/kg per day of a cytokine can be administered to a human subject. However, the precise determination of what would be considered an effective dose may be based on factors individual to each patient, including their size, age, disease or injury, size damage, amount of time since the damage occurred and factors associated with the mode of delivery (direct injection—lower doses, intravenous—higher doses). An issue regarding the use of stem cells is the purity of the population. Bone marrow cells, for example, comprise mixed populations of cells, which can be purified to a degree sufficient to produce a desired effect. Those skilled in the art can readily determine the percentage of MAPCs in a population using various well-known methods, such as fluorescence activated cell sorting (FACS). Preferable ranges of purity in populations comprising MAPCs, or there differentiated progeny, are 50-55%, 55-60%, and 65-70%. More preferably the purity is 70-75%, 75-80%, 80-85%; and most preferably the purity is 85-90%, 90-95%, and 95-100%. However, populations with lower purity can also be useful, such as about 25-30%, 30-35%, 35-40%, 40-45% and 45-50%. Purity of MAPCs can be determined according to the gene expression profile within a population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, MAPCs, or differentiated progeny thereof, can be administered initially, and thereafter maintained by further administration of MAPCs or differentiated progeny thereof. For instance, MAPCs can be administered by one method of injection, and thereafter further administered by a different or the same type of method. For example, MAPCs can be administered by surgical injection to bring lung function to a suitable level. The patient's levels can then be maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising MAPCs, or differentiated progeny thereof, include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs as described in the present invention.

Compositions can be administered in dosages and by techniques available to those skilled in the medical and veterinary arts taking into consideration such factors as the age, sex, weight, and condition of the particular patient, and the composition form used for administration (e.g., solid vs. liquid).

Suitable regimes for initial administration and further doses or for sequential administrations also are variable, may include an initial administration followed by subsequent administrations.

Approaches for Transplantation to Prevent Immune Rejection

In some embodiments, it may be desired that the MAPCs (or differentiated progeny thereof) be treated or otherwise altered prior to transplantation/administration in order to reduce the risk of stimulating host immunological response against the transplanted cells. Any method known in the art to reduce the risk of stimulating host immunological response may be employed. The following provides a few such examples.

1. Universal donor cells: MAPCs have cell surface profiles consistent with evasion of immune recognition, and in their natural state may not stimulate immune sensitization and rejection. They may serve as natural universal donor cells even if their progeny mature to cells which ordinarily would be immune recognized and rejected.

Alternatively, MAPCs can be manipulated to serve as universal donor cells. Although undifferentiated MAPCs do not express HLA antigens, some differentiated progeny may express one or both of these antigens. MAPCs can be modified to serve as universal donor cells by eliminating HLA type-I or HLA-type-II antigens, and potentially introducing the HLA-antigens from the prospective recipient so that the cells do not become easy targets for NK-mediated killing, or become susceptible to unlimited viral replication and/or malignant transformation. Elimination of HLA-antigens can be accomplished by homologous recombination or by introduction of point-mutations in the promoter region or by introduction of a point mutation in the initial exon of the antigen to introduce a stop-codon, such as with chimeroplasts. Transfer of the host HLA-antigen(s) can be achieved by retroviral, lentiviral, adeno associated virus or other viral transduction or by transfection of the target cells with the HLA-antigen cDNAs.

2. Intrauterine transplant to circumvent immune recognition: MAPCs can be used in an intrauterine transplantation setting to correct genetic abnormalities, or to introduce cells that will be tolerated by the host prior to immune system development. This can be a way to make human cells in large quantities in animals or it could be used as a way to correct human embryo genetic defects by transplanting cells that make the correct protein or enzyme.

3. Development of Hematopoietic Cells: MAPCs can be administered (e.g., intravenously) to establish hematopoiesis (the process by which blood cells are formed). Once the administered MAPCs have generated blood cells and the subject has accepted the blood type of MAPC derived blood cells, the subject may no longer reject additional MAPCs or progeny or tissue derived therefrom.

4. Encapsulation: In some embodiments, the MAPCs are encapsulated. The primary goal in encapsulation as a cell therapy is to protect allogeneic and xenogeneic cell transplants from destruction by the host immune response, thereby eliminating or reducing the need for immuno-suppressive drug therapy. Techniques for microencapsulation of cells are known to those of skill in the art (see, for example, Chang, P., et al., *Trends in Biotech.*, 17:78-83 (1999); Matthew, H. W., et al., *ASAIO Trans*, 37(3):M328-30 (1991); Yanagi, K., et al., *ASAIO Trans.*, 35(3):570-2 (1989); Cai Z. H., et al., *Artif Organs*, 12(5):388-93 (1988); Chang, T. M., *Artif Organs*, 16(1):71-4 (1992)). Materials for microencapsulation of cells include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

Additionally, the MAPCs may be encapsulated by membranes prior to implantation. The encapsulation provides a barrier to the host's immune system and inhibits graft rejection and inflammation. It is contemplated that any of the many methods of cell encapsulation available may be employed. In some instances, cells are individually encapsulated. In other instances, many cells are encapsulated within the same membrane. In embodiments in which the cells are removed following implantation, the relatively large size of a structure encapsulating many cells within a single membrane provides a convenient means for retrieval of the implanted cells. Several methods of cell encapsulation are available to the art, such as those described in European Patent Publication No. 301,777 or U.S. Pat. Nos. 4,353,888; 4,744,933; 4,749,620; 4,814,274; 5,084,350; 5,089,272; 5,578,442; 5,639,275; and 5,676,943, each of which is incorporated herein by reference.

5. Natural Killer (NK) Cell Function: Any means which inhibits NK cell function or depletes NK cells from a population of cells may also be administered to prevent immune rejection, increase engraftment and/or increase immune tolerance. Such an agent includes an anti-NK cell antibody or irradiation or any other material which can inhibit NK cell function or deplete NK cells from a population.

Monitoring of Subject after Administration of MAPCs

Following transplantation, the growth and/or differentiation of the administered MAPCs or differentiated progeny, and the therapeutic effect of the MAPCs or progeny may be monitored. For example, the functionality of MAPCs administered to treat a lung disorder may be monitored by analyzing total lung capacity, flow rate, oxygen and/or gas levels in blood or a chest x-ray. For example an increase in total lung capacity or flow rate of a subject following administration of MAPCs, or differentiated progeny thereof, is indicative of functionality.

Following administration, the immunological tolerance of the subject to the MAPCs or progeny derived therefrom may be tested by various methods known in the art to assess the subject's immunological tolerance to MAPCs. In cases where subject tolerance of MAPCs is suboptimal (e.g., the subject's immune system is rejecting the exogenous MAPCs), therapeutic adjunct immunosuppressive treatment, which is known in the art, of the subject may be performed.

Genetically-Modified MAPCs

MAPCs or differentiated progeny derived therefrom can be genetically altered ex vivo, eliminating one of the most significant barriers for gene therapy. For example, a subject's bone marrow aspirate is obtained, and from the aspirate MAPCs are isolated. The MAPCs are then genetically altered to express one or more desired gene products. The MAPCs can then be screened or selected ex vivo to identify those cells which have been successfully altered, and these cells can be introduced into the subject or can be differentiated and introduced into the subject, either locally or systemically. Alternately, MAPCs can be differentiated and then the differentiated cells can be genetically altered prior to administration. In either case, the transplanted cells provide a stably-transfected source of cells that can express a desired gene product. Genetically-modified MAPCs or genetically-modified differentiated progeny derived therefrom are useful in the methods of the invention, for example, in the treatment of genetic disorders, including but not limited to mucoviscidosis (cystic fibrosis) and immotile cilia syndrome, or to provide a gene product to a desired tissue (e.g., lung tissue).

A. Methods for Genetically Altering MAPCs

MAPCs, or differentiated progeny derived therefrom, can be genetically modified by introducing DNA or RNA (e.g., an exogenous nucleic acid) into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, nucleofection, or direct "naked"

DNA transfer. Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

51. Homologous Recombination

Calcium phosphate transfection, which relies on precipitates of plasmid DNA/calcium ions, can be used to introduce plasmid DNA containing a target gene or polynucleotide into isolated or cultured MAPCs. Briefly, plasmid DNA is mixed into a solution of calcium chloride, and then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

Cells can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPE) can be added. A recommended reagent for liposomal transfer is Lipofectin® (Life Technologies, Inc.), which is commercially available. Lipofectin®, for example, is a mixture of the cationic lipid N-[1-(2,3-dioleyloyx)propyl]-N-N-N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al., 1998).

Gene transfer techniques which have been shown effective for delivery of DNA into primary and established mammalian cell lines using lipopolyamine-coated DNA can be used to introduce target DNA into MAPCs and the vascular endothelial cells of the invention. This technique is generally described by Loeffler, J. and Behr, J., 1993).

Naked plasmid DNA can be injected directly into a tissue mass formed of differentiated cells, such as the vascular endothelial cells of the invention. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into cells either in vitro or in vivo. The basic procedure for microprojectile gene transfer was described by J. Wolff in "Gene Therapeutics" (1994) at page 195. Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated MAPCs. Microparticle injection techniques have been described previously, and methods are known to those of skill in the art (see Johnston, S. A., et al., 1993; Williams, R. S., et al., 1991; Yang, N. S., et al., 1990.

Signal peptides can be attached to plasmid DNA, as described by Sebestyen, et al. (1998), to direct the DNA to the nucleus for more efficient expression.

Viral vectors are used to genetically alter MAPCs and their progeny, including the vascular endothelial cells of the invention. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., 1998. Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5 to the SV40 promoter, which is operationally linked to the target gene sequence cloned into the multicloning site, followed by a 3'second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al. (1999), who used single-chain variable fragment antibody directed against the surface glycoprotein high-molecular-weight melanoma-associated antigen fused to the amphotropic murine leukemia virus envelope to target the vector to delivery the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the MAPCs, such as markers expressed by the vascular endothelial cells of the invention, can be used to target delivery to those cells.

Lentiviral vectors are also used to genetically alter MAPCs and the vascular endothelial cells of the invention. Many such vectors have been described in the literature and are known to those of skill in the art. (Salmons, B. and Gunzburg, W. H., 1993). These vectors have been effective for genetically altering human hematopoietic stem cells (Sutton, R., et al., 1998). Packaging cell lines have been described for lentivirus vectors (see Kafri, T., et al., 1999; Dull, T., et al., 1998).

Recombinant herpes viruses, such as herpes simplex virus type I (HSV-1) have been used successfully to target DNA delivery to cells expressing the erythropoietin receptor (Laquerre, S., et al., 1998). These vectors can also be used to genetically alter the MAPCs or the vascular endothelial cells of the invention, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (see, for example, Davidson, B. L., et al., 1993; Wagner, E., et al., 1992). Methods for inserting target DNA into an adenovirus vector are known to those of skill in the art of gene therapy, as are methods for using recombinant adenoviral vectors to introduce target DNA into specific cell types (see Wold, W., *Adenovirus Methods and Protocols*, Humana Methods in Molecular Medicine (1998), Blackwell Science, Ltd.). Binding affinity for certain cell types has been demonstrated by modification of the viral vector fiber sequence. Adenovirus vector systems have been described which permit regulated protein expression in gene transfer (Molin, M., et al., 1998). A system has also been described for propagating adenoviral vectors with genetically modified receptor specificities to provide transductional targeting to specific cell types (Douglas, J., et al., 1999). Recently described ovine adenovirus vectors even address the potential for interference with successful gene transfer by preexisting humoral immunity (Hofmann, C., et al., 1999).

Adenovirus vectors are also available which provide targeted gene transfer and stable gene expression using molecular conjugate vectors, constructed by condensing plasmid DNA containing the target gene with polylysine, with the polylysine linked to a replication-incompetent adenovirus (Schwarzenberger, P., et al., 1997).

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al., 1989; Bredenbeek, P. J., et al., 1993; and Frolov, I., et al., 1996).

MAPCs possess good transduction potential using the eGFP-MND lentiviral vector described by Robbins, et al. (1997) and eGFP-MGF vector. Using this method, 30-50% of MAPCs can be transduced after a short exposure of 4.6 hours to an enhanced green fluorescent protein (eGFP) vector containing supernatants made in PA3-17 packaging cells (an amphotropic packaging cell line derived from NIH 3T3 fibroblasts and described by Miller, A. D., and C. Buttimore (1986), combined with protamine (8 mg/ml). Expression of eGFP persists throughout the culture of undifferentiated MAPC. In addition, transfection using lipofectamine has been successfully used to introduce transgenes in MAPCs.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., 1998). Alternative selectable markers include the β-Gal gene, the truncated nerve growth factor receptor, drug selectable markers (including but not limited to NEO, MTX, hygromycin).

Any of these techniques can also be applied to introduce a transcriptional regulatory sequence into MAPCs to activate a desired endogenous gene. This can be done by both homologous (e.g., U.S. Pat. No. 5,641,670) or non-homologous (e.g., U.S. Pat. No. 6,602,686) recombination. These are incorporated by reference for teaching of methods of endogenous gene activation.

The present invention is additionally described by way of the following illustrative, non-limiting Example, which provides a better understanding of the present invention and of its many advantages.

EXAMPLE

This invention is further illustrated by the following example, which is not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Differentiation of MAPCs to Type II Alveolar Epithelial Cells

Murine MAPCs were isolated from ROSA26 murine bone marrow (Jiang, Y. et al, (2002) Nature 418: 41-49). Briefly, bone marrow (BM) was obtained from ROSA26 mice (age 6-8 weeks) and bone marrow mononuclear cells (BMMNCs) were plated on fibronectin (FN; 11 g/mL) in expansion medium with 10 ng/mL EGF (Sigma), 10 ng/mL PDGF-BB (R&D Systems) and 2 U/mL LIF (Chemicon). After about 3 weeks, remaining CD45$^-$/Ter119$^-$ cells were selected (about 20% of all cells), cells were subcultured at 10 cells/well, and were maintained between 0.5-1.5×10$^3$ cells/cm$^2$. Approximately 1% of wells seeded with 10 CD45$^-$/TER119$^-$ cells yielded continuous growing cultures.

The cells were cultured in MAPC expansion medium, which comprises 60% DMEM-Low glucose, 40% MCDB-201 with IX insulin-transferrin-selenium (ITS), 1× linoleic acid-bovine serum albumin (LA-BSA), 10$^{-9}$M dexamethasone, 10$^4$M ascorbic acid 2-phosphate, 100 units of penicillin and 1000U streptomycin with 2% fetal calf serum (FCS) with 2 U/mL leukemia inhibitory factor (LIF), 10 ng/ml epidermal growth factor (EGF), and 10 ng/ml platelet derived growth factor-BB (PDGF-BB).

Differentiation of MAPCs into lung epithelial cells was carried out according to standard procedures in the art described in Tissue Engineering, Vol. 8, page 541 (2002). Cells were allowed to adhere onto Greiner Bio-One plates coated with 0.01 μg/ml of fibronectin in sterile PBS. MAPCs were subsequently cultured in the absence of leukemia inhibitory factor (LIF) for 30 days to promote differentiation. Cells were passaged 1:3 on days 10, 20, and 30 by aspirating media, adding 5 ml of 1× Trypsin-EDTA solution (Cellgro 25-052-CI; Mediatech, Inc.). Cells were observed on inverted scope until they released from the plate. Supplemental media was added to deactivate trypsin (15 ml) and the cells were placed in a 50 ml conical tube and spun down for 10 min at 1200 rpm. The media was then aspirated. The pellet was resuspended in 10 ml of appropriate media. The cells were again placed in a 50 ml conical tube and spun down for 10 min at 1200 rpm. The media was then aspirated and the cells resuspended and divided onto new plates.

The MAPCs were then transferred to Small Airway Growth Medium (SAGM) (SAGM BullitKit, Cambrex #CC-3118) for an additional 14 days. Cells grown in SAGM stained positively for pro-Surfactant protein C (pro-SPC) by immunofluorescence and were positive by reverse transcription-polymerase chain reaction (RT-PCR) for FGFR2-IIIb that binds keratinocyte growth factor (KGF), consistent with alveolar type II (ATII) cells. MAPCs cultured in MAPC medium in the absence of LIF during the same time period were negative for both SP-C and KGF receptor (KGFR).

Differentiated MAPCs were subjected to immunofluorescence analysis by obtaining 20,000 to 50,000 cells in 100 μl of medium for 3 minutes at 1000 rpm. Slides were blocked with 10% normal horse serum in PBS for 20 minutes. A pro-SPC rabbit antibody (Chemicon AB3428) diluted 1:500 in blocking solution was used, followed by donkey anti-rabbit Cy5 conjugated secondary antibodies diluted 1:500 in blocking solution for 30 minutes. FIG. 1 shows that while MAPCs grown in MAPC medium do not express pro-SPC, growth in SAGM promotes the expression of pro-SPC. As a positive control, cryosections of normal mouse lung were used to show the expected frequency of SPC-positive ATII cells. Cells that were stained only with the secondary Cy5 antibody also did not show staining characteristic of pro-SPC staining.

For RT-PCR analyses, cells were placed in Trizol reagent and isolated by standard protocols (Invitrogen, Carlsbad, Calif.). Quantitation of RNA was performed by fluorescence readings at λ=260/280 nm on a Beckman DU640 spectrophotometer. After the samples were normalized to equal 2 μg, the RNA samples were denatured at 70° C. for 5-10 minutes. RNAsin (Invitrogen) was added and the sample spun after incubation to collect condensation. In a total volume of 30 μl, the following reagents were added to the RNA sample: 2 μl of primers, 6 μl of 5× reaction buffer (Invitrogen), 0.6 μl of 25 mM dNTPs, 0.9 μl of 0.1M DTT, and 2 μl of Superscript II. The reaction was incubated at 42° C. for 1 hour, followed by termination at 70° C. for 10 minutes. DEPC-treated water was added to the sample, and stored at −20° C. The following primers and the PCR conditions are provided in Table 2.

TABLE 2

| Primer | Primer Sequences | PCR Program |
|---|---|---|
| HPRT sense | 5'-GTTGGATACAGGCCAGACT TTGTTG-3' (SEQ ID NO: 1) | 0 min at 94° C. |
| HPRT anti-sense | 5'-TCGGTATCCGGTCGGATGG GAG-3' (SEQ ID NO: 2) | 0 min at 50° C. 20 min at 72° C. repeat 40 cycles |
| FGFR2-IIIb specific | 5'-AGGCGACTGGTTGGCCTG-3' (SEQ ID NO: 3) | 0 min at 94° C. |
| FGFR2-IIIb constant | 5'-AACGGTCACCACACCGGC-3' (SEQ ID NO: 4) | 0 min at 50° C. 20 min at 72° C. repeat 40 cycles |

Figure 2:
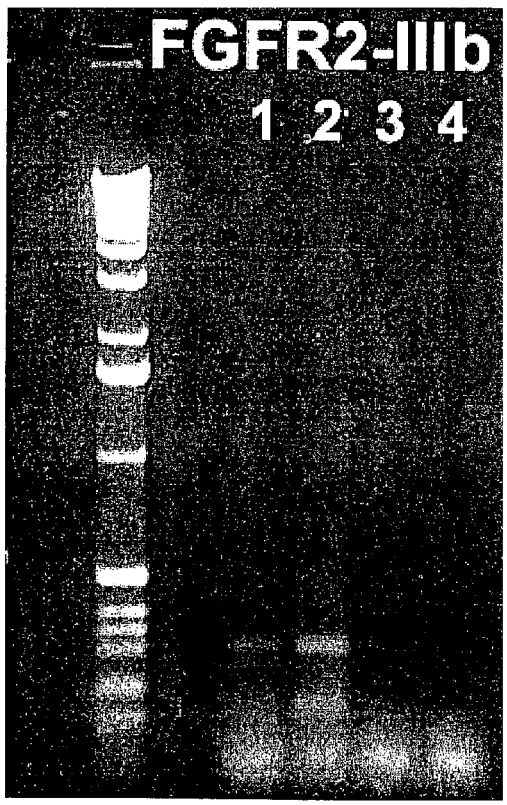
FIG. 2 shows electrophoretically separated fragments of reverse-transcribed DNA corresponding to FGFR2-IIIb (left panel) and a positive control housekeeping gene, HPRT (right panel). MAPCs cultured in MAPC medium are represented by lane 3. Normal C57BL/6 mouse lung was used as a positive control and is shown in lane 1. MAPCs cultured in SAGM are shown in lane 2.
Figure 2:
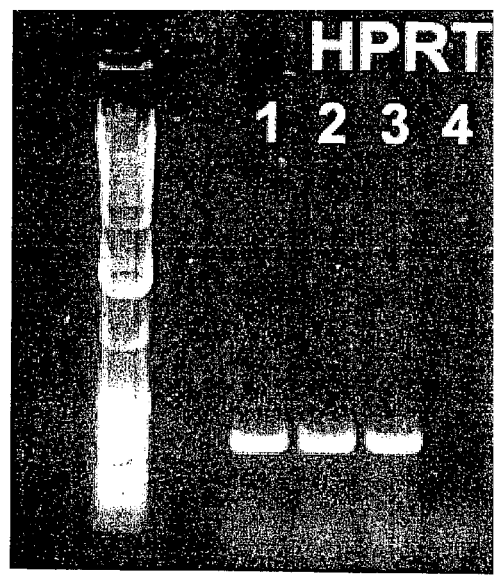

PCR products were analyzed on a 1.5% agarose gel containing ethidium bromide in 1× tris-acetate-EDTA buffer. FIG. 2 depicts RT-PCR analyses of MAPCs grown as indicated in FIG. 1 in SAGM, which were positive by RT-PCR for the fibroblast growth factor receptor FGFR2-IIIb that binds keratinocyte growth factor. This observation is consistent with alveolar type II cells (left panel, lane 2). MAPCs cultured in MAPC medium in the absence of LIF during the same time period were negative for FGFR2-IIIb. Normal C57BL/6 murine lung was used as a positive control and shows the expected FGFR2-IIIb band (left panel, lane 1). The right panel represents a housekeeping gene control (HPRT) for DNA loading and integrity of the samples. There was no difference among the samples for HPRT.

BIBLIOGRAPHY

Abe, A., et al., *J. Virol.* 1998; 72: 6159-6163.
Babcook, et al., *Proc. Natl. Acad. Sci. (USA)*. 1996; 93: 7843-7848.
Basch, et. al., *J. Immunol. Methods*. 1983; 56:269.
Batinic, D., et al., *Bone Marrow Transplant*. 1990; 6(2):103-7.

Bird, et al., *Science.* 1988; 242:423-426.
Bittira B, et al. *Eur J Cardiothorac Surg.* 2003; 24:393-398.
Borue X, et al. *Am J Pathol.* 2004; 165:1767-1772.
Bredenbeek, P. J., et al. *J. Virol.* 1993; 67:6439-6446.
Cai Z. H., et al., *Artif Organs.* 1988; 12(5):388-93.
Chang, P., et al., *Trends in Biotech.* 1999; 17:78-83.
Chang, T. M., *Artif Organs.* 1992; 16(1):71-4.
Clackson et al. *Nature.* 1991; 352:624-628.
Clarke, *Science.* 2000; 288:1660-3.
Clothia et al., *J. Mol. Biol.* 11985; 186:651-66, 1985.
Coligan, et al., *Current Protocols in Immunology*, (1991 and 1992).
Davidson, B. L., et al., *Nature Genetics.* 1993; 3:219-223.
Douglas, J., et al. *Nature Biotech.* 1999; 17:470-475.
Drukker M, et al. *Proc Natl Acad Sci USA.* 2002; 99:9864-9869.
Dull, T., et al., *J. Virol.* 1998; 72:8463-8471.
Ferrari, *Science.* 1998; 279:528-30.
Frolov, I., et al. (*Proc. Natl. Acad. Sci. USA.* 1996; 93:11371-11377.
Gussoni, *Nature.* 1999; 401:390-4.
Hofmann, C., et al. *J. Virol.* 1999; 73:6930-6936.
Hollinger et al., *Proc. Natl. Acad Sci. USA.* 1993; 906444-6448 (1993).
Holmes, et al., *J. Immunol.* 1997; 158:2192-2201.
Jackson, PNAS USA. 1999; 96:14482-6.
Jahagirdar, B. N., et al. *Exp Hematol.* 2001; 29(5):543-56.
Jiang Y, et al., *Proc Natl Acad Sci USA.* 2003; 100 Suppl 1:11854-11860.
Jiang Y, et al., *Nature.* 2002a; 418:41-49.
Jiang Y, et al., *Exp Hematol.* 2002b; 30:896-904.
Johnston, S. A., et al., *Genet. Eng.* (NY) 1993; 15: 225-236.
Jones et al., *Nature.* 1986; 321:522-525.
Kawada H, et al. *Blood.* 2004; 104:3581-3587.
Kohler & Milstein, *Nature.* 1975; 256:495.
Krause D S, et al. *Cell.* 2001; 105:369-377.
Lagasse E, et al. *Nat Med.* 2000; 6:1229-1234.
Lanier L L. "NK Cell Recognition." *Annu Rev Immunol.* 2004.
Laquerre, S., et al. *J. Virol.* 1998; 72:9683-9697.
Larrick, et al., *Methods: A Companion to Methods in Enzymology.* (1991).
Lim, J. W. and Bodnar, A., *Proteomics.* 2002; 2(9):1187-1203 (2002).
Loeffler, J. and Behr, J., *Methods in Enzymology.* 1993; 217: 599-618.
Kafri, T., et al., *J. Virol.* 1999; 73:576-584.
Marks et al., *J. Mol Biol.* 1991; 222:581-597.
Martin, F., et al., *J. Virol.* 1999; 73:6923-6929.
Matthew, H. W., et al., *ASAIO Trans.* 1991; 37(3):M328-30.
Miller, A. D., and C. Buttimore, *Mol. Cell. Biol.* 1986; 6:2895-2902.
Mochizuki, H., et al., *J. Virol.* 1998; 72:8873-8883.
Molin, M., et al. *J. Virol.* 1998; 72:8358-8361.
Morrison et al. *Proc. Natl. Acad Sci.* 1984; 81, 6851-6855.
Muschler, G. F., et al. *J Bone Joint Surg. Am.* 1997; 79(11): 1699-709.
Novotny and Haber, *Proc. Natl. Acad. Sci. USA.* 1985; 82; 4592-4596.
Pack, et al., *Bio/Technology.* 1993; 11:1271-77.
Persons, D., et al., *Nature Medicine.* 1998; 4: 1201-1205.
Petersen, *Science.* 1999; 284:1168-1170.
Presta, *Curr. Op. Struct. Biol.* 1992; 2:593-596.
Reichmann et al., *Nature.* 1988; 332:323-329.
Reyes, M. et al. *Blood.* 2001; 98; 2615-2625.
Reyes M, et al., *J Clin Invest.* 2002; 109:337-346.
Reyes M, and Verfaillie CM. *Ann N Y Acad Sci.* 2001; 938: 231-233; discussion 233-235.
Robbins, et al. *J. Virol.* 1997; 71(12):9466-9474.
Salmons, B. and Gunzburg, W. H., 1993; 4:129-141.
Sebestyen, et al. *Nature Biotech.* 1998; 16:80-85.
Schwartz R E, et al. *J Clin Invest.* 2002; 109:1291-1302.
Schwarzenberger, P., et al., *J. Virol.* 1997; 71:8563-8571.
Shimazaki T., et al., EMBO J. 1993; 12(12):4489-98.
Sutton, R., et al., *J. Virol.* 1998; 72:5781-5788.
Takahashi, *Nat Med.* 1999; 5:434-8.
Takahashi, *J Clin Invest.* 2000; 105:71-7.
Theise, *Hepatology.* 2000a; 31:235-40.
Theise, *Hepatology.* 2000b; 32:11-6.
Vaswani, et al., Annals Allergy, Asthma & Immunol. 1998; 81:105-115.
Verfaillie, C. M. Trends Cell Biol. 2002; 12(11):502-8.
Wagers A J, et al. *Science.* 2002; 297:2256-2259.
Wagner, E., et al., *Proc. Natl. Acad. Sci. USA.* 1992; 89:6099-6103.
Williams, R. S., et al., *Proc. Natl. Acad. Sci. USA.* 1991; 88:2726-2730.
Whitlow, et al., *Methods: A Companion to Methods in Enzymology* (1991).
Wold, W., Adenovirus Methods and Protocols, Humana Methods in Molecular Medicine (1998), Blackwell Science, Ltd.
Wu G D, et al. *Transplantation.* 2003; 75:679-685.
Wysocki and Sato, *Proc. Natl. Acad. Sci. (USA).* 1978; 75:2844.
Xiong, C., et al., *Science.* 1989; 243:1188-1191.
Yanagi, K., et al., *ASAIO Trans.* 1989; 35(3):570-2.
Yang, N. S., et al., *Proc. Natl. Acad. Sci. USA.* 1990; 87:9568-9572.
Zhao L R, et al. *Exp Neurol.* 2002; 174:11-20.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to produce alveolar type II epithelial cells (1) in vitro by exposing cells (2) in vitro to factors that result in differentiation of said cells (2) to cells with an alveolar type II epithelial phenotype (1), said cells (2) being isolated expanded human multipotent non-embryonic non-germ cells that can differentiate into at least one cell type of each of the endodermal, ectodermal, and mesodermal embryonic lineages and express telomerase, said cells have undergone at least 10-40 cell doublings in culture, so as to produce cells with an alveolar type II epithelial phenotype (1).

2. The method of claim 1 further comprising isolating the differentiated alveolar type II epithelial cells.

3. The method of claim 1 further comprising growing the alveolar type II epithelial cells in culture medium.

4. The method of any of claims 1-3 further comprising mixing an effective therapeutic amount of the alveolar type II epithelial cells with a pharmaceutically acceptable carrier.

* * * * *

UNITED STATES PATENT AND TRADEMARK OFFICE
CERTIFICATE OF CORRECTION

PATENT NO. : 8,609,412 B2  Page 1 of 1
APPLICATION NO. : 11/587511
DATED : December 17, 2013
INVENTOR(S) : Panoskaltsis-Mortari et al.

It is certified that error appears in the above-identified patent and that said Letters Patent is hereby corrected as shown below:

In the Specification

In Column 1, lines 33 - 35, please delete the two (2) sentences,

"This work was funded by United States Grant No. RO1-HL55209-05 from the Naitonal Institutes of Health. The government may have certain rights to this invention."

and insert

-- This invention was made with government support under R01-HL055209-05 awarded by the National Institutes of Health. The government has certain rights in the invention. --

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,609,412 B2
APPLICATION NO.  : 11/587511
DATED            : December 17, 2013
INVENTOR(S)      : Panoskaltsis-Mortari et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1968 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: A synthetic primer

```
<400> SEQUENCE: 1
gttggataca ggccagactt tgttg                                              25

<210> SEQ ID NO 2
<211> LENGTH: 22
<212> TYPE: DNA
<213> ORGANISM: Artificial Sequence
<220> FEATURE:
<223> OTHER INFORMATION: A synthetic primer

<400> SEQUENCE: 2
tcggtatccg gtcggatggg ag                                                 22

<210> SEQ ID NO 3
<211> LENGTH: 18
<212> TYPE: DNA
<213> ORGANISM: Artificial Sequence
<220> FEATURE:
<223> OTHER INFORMATION: A synthetic primer

<400> SEQUENCE: 3
aggcgactgg ttggcctg                                                      18

<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
aacggtcacc acaccggc                                                      18
```